United States Patent [19]

Clarke

[11] Patent Number: 5,239,180

[45] Date of Patent: Aug. 24, 1993

[54] LASER SYSTEMS FOR FOOD ANALYSIS BASED ON REFLECTANCE RATIO DETECTION

[75] Inventor: Richard H. Clarke, Scituate, Mass.

[73] Assignee: Boston Advanced Technologies, Inc., Newton, Mass.

[21] Appl. No.: 928,539

[22] Filed: Aug. 13, 1992

Related U.S. Application Data

[63] Continuation of Ser. No. 750,423, Aug. 14, 1991, abandoned, which is a continuation of Ser. No. 473,917, Feb. 2, 1990, abandoned.

[51] Int. Cl.$^5$ .................. G01N 21/27; G01N 21/33
[52] U.S. Cl. ............................. 250/339; 250/341; 356/51; 356/407; 356/425
[58] Field of Search ............... 356/402, 407, 420, 425, 356/51, 39, 40, 41; 250/339, 341; 204/577, 580, 581, 582

[56] References Cited

U.S. PATENT DOCUMENTS

| | | | |
|---|---|---|---|
| 3,750,883 | 8/1973 | Irving et al. | 356/407 |
| 4,057,352 | 11/1977 | Babb | 356/407 |
| 4,169,676 | 10/1979 | Kaiser | 356/39 |
| 4,202,339 | 5/1980 | Wirtzfeld et al. | 128/419 |
| 4,223,680 | 9/1980 | Jobsis | 128/633 |
| 4,350,163 | 9/1982 | Ford, Jr. et al. | 128/633 |
| 4,408,880 | 10/1983 | Tsuji et al. | 356/338 |
| 4,476,982 | 10/1984 | Paddock et al. | 209/582 |
| 4,558,786 | 12/1985 | Lane | 209/577 |
| 4,566,797 | 1/1986 | Kaffka et al. | 356/420 |
| 4,805,623 | 2/1989 | Jöbsis | 356/320 |
| 4,822,568 | 4/1989 | Tomita | 356/39 |
| 4,882,492 | 11/1989 | Schlager | 250/346 |

FOREIGN PATENT DOCUMENTS 0160768 11/1985 European Pat. Off. .
221642 5/1987 European Pat. Off. ............ 356/407
282210 9/1988 European Pat. Off. .
0282234 9/1988 European Pat. Off. .
0404562 12/1990 European Pat. Off. .
9007905 7/1990 PCT Int'l Appl. .

OTHER PUBLICATIONS

Wilson et al., "Circulation," vol. 80, pp. 1668-1674 (1989).
Polanyi et al., "In Vivo Oximeter with Fast Dynamic Response" vol. 33 Review of Scientific Instruments, pp. 1050-1054 (1962).
Steinke et al., "Reflectance measurements of hematocrit and oxyhemoglobin saturation" vol. 363, American Journal of Physiology, pp. H147-H153 (1987).
Peuchant et al., "Determination of Serum Cholesterol by Near-Infrared Reflectance Spectrometry," Analytical Chemistry, vol. 59 pp. 1819-1825 (1987).
Osborne, "Applications of NIR in the Baking Industry," vol. 20 Analytical Procedures, pp. 79-83 (1983).
Giangiacomo et al., "Predicting Concentrations of Individual Sugars in Dry Mixtures," vol. 46, Journal of Food Science, pp. 531-534 (1981).

Primary Examiner—F. L. Evans
Attorney, Agent, or Firm—Thomas J. Engellenner; James E. Maslow

[57] ABSTRACT

Systems and methods for material analysis are disclosed in which a material (e.g., a food of food ingredient) is illuminated at a plurality of discrete wavelengths. Measurements of the intensity of reflected light at such wavelengths are taken, and a analysis of reflection ratios for various wavelengths is performed. Changes in the reflection ratios are correlated with specific material properties such as the concentration of analytes or the condition of the material (e.g., spoilage, ripeness, degree of cooking or other processing stages).

4 Claims, 4 Drawing Sheets

LASER SYSTEMS FOR FOOD ANALYSIS BASED ON REFLECTANCE RATIO DETECTION

This application is a continuation of application Ser. No. 07/750,423, filed Aug. 14, 1991, now abandoned, which is a continuation of Ser. No. 07/473,917 filed on Feb. 2, 1990, now abandoned.

BACKGROUND OF THE INVENTION

The technical field of this invention is material analysis and, in particular the invention relates to the detection and quantification of analytes in foods by measuring reflectivity at multiple wavelengths.

Material analysis, especially the analysis of foods for the presence of contaminants and/or degradation products, can be a tedious and complex task. In many instances it would be more desirable to be able to analyze such materials quickly, easily, and non-destructively. One example of such an application is meat analysis.

Conventionally, meats and other foods are analyzed by extracting a sample and examining it using one or more techniques such as immunoassays, activity assays, chromotographic assays, and spectrophotometric assays. These conventional methods all suffer from several common disadvantages. One such disadvantage is that it usually takes some time to perform tests on the sample, the length of time being dependent on the complexity of the test. This time delay between when the sample is taken and when the analysis is completed provides a window during which the food's content may have changed, leading to erroneous test results.

Additionally, situations arise when repeated monitoring is desirable, for example when monitoring daily changes in the freshness of refrigerated meats and the like. Similarly, continuous measurements can be desirable in monitoring the cooking or other preparatory steps in food processing.

In the absence of reliable and rapid measurement techniques, wholesome foodstuffs often must be destroyed because arbitrary shelf-life or refrigeration limitations have expired. Likewise, in the absence of careful attention, foods can be ruined due to overcooking or other errors during processing.

Accordingly, it is the object of the present invention to provide an analytic apparatus for non-destructively, quickly, and easily detecting and quantifying analytes in a material.

It is another object of this invention to provide an analytic apparatus particularly adapted for detecting and quantifying the state or condition of foods in such a way as to avoid the problems of stale test results and food waste.

SUMMARY OF THE INVENTION

Systems and methods for material analysis are disclosed in which food materials are analyzed by illumination at a plurality of discrete wavelengths. (As used herein, the term "food material" is intended to encompass and include, without limitation, meats, poultry, fish and other seafood, fruits, vegetables, cereals. grains and seeds, dairy products, and beverages as well as food extracts, ingredients, nutrients and/or additives). Measurements of the intensity of light reflected by the food material at such wavelengths are taken, and an analysis of reflection ratios for various wavelengths is performed. Changes in the reflection ratios can be correlated with the concentration of analytes in the sample and thereby used to determine the condition of the food material (e.g., oxidation, contamination, sugar content, ripeness, fermentation, degree of cooking, or other processing stages).

In one aspect of the invention, an analytical apparatus and methods are described employing a multi-wavelength illumination source, a wavelength specific detector array, and a reflection ratio analyzer. The illumination source illuminates a material sample at a plurality of discrete wavelengths. The detector array detects the light reflected from the sample, converts the detected light into electrical signals indicative of the intensity of the reflected light at each wavelength, and transmits the converted signals to a reflection ratio analyzer. The reflection ratio analyzer then derives a reflectance ratio for at least two of the detected wavelengths, such that the ratio can be compared with predetermined values to detect the presence of an analyte in a material sample.

In one illustrated embodiment of the invention the illumination source further comprises at least two laser diodes, producing light at distinct wavelengths, spanning at least a portion of a spectrum from about 500 nm to about 2000 nm, preferably from about 600 nm to about 1500 nm. This embodiment is particularly well suited to provide a system for detecting analytes in red meats and other foods, and for monitoring the cooking or other processing steps in the preparation of foods.

The present invention is an improvement over the prior art in that it can non-destructively, quickly and easily detect and/or quantify analytes in foods and other material samples. In this way, the invention eliminates the problems of stale test data and needless inventory destruction, as well as provides a simple and easy method for monitoring food preparation.

The invention will next be described in connection with certain preferred embodiments; however, it should be clear that various additions, subtractions and modifications can be made without departing from the spirit or scope of the invention. For example, although the invention is illustrated in connection with a food analysis system, various alternative embodiments can also be devised, such as systems for monitoring liquid materials, generally, including oils, beverages, blook, chemicals and the like.

Additionally, although the illustrated embodiment shows a system with a fiber optic bundle for delivery of six distinct wavelengths of light, it should be clear that the number of interrogation wavelengths, the size and shape of the sampling head and the means for transmitting the light to and from the sample can be varied to meet particular needs and applications. Moreover, although lasers are described as preferred light sources, other illumination means including a non-coherent, discrete wavelength light sources can be employed.

DETAILED DESCRIPTION

Figure 1:
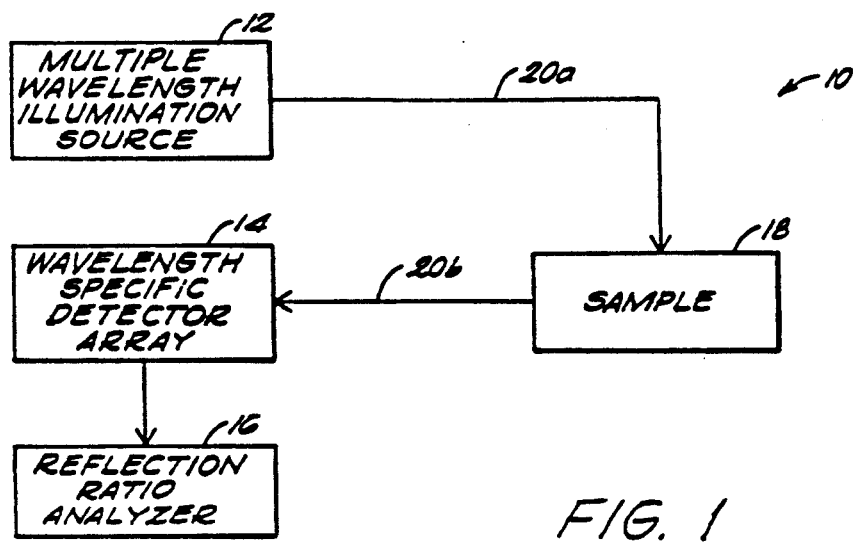
FIG. 1 is a schematic block diagram of an analytic apparatus according to the invention.

A schematic block diagram of an analytic apparatus 10 according to the invention is shown in FIG. 1. Apparatus 10 includes a multiple wavelength illumination source 12, a wavelength specific detector array 14, and a reflection ratio analyzer 16. Illumination source 12 illuminates the material sample 18 at a plurality of wavelengths via optical path 20a. Detector array 14 detects light reflected from sample 18 through optical path 20b. The detector array 14 converts the reflected light into electrical signals indicative of the intensity of the reflected light at each wavelength and transmits the converted signals to the reflection ratio analyzer 16 which processes the electrical signals and derives a reflectance ratio for at least two of the wavelengths transmitted. Analyzer 16 then compares the calculated reflectance ratio with predetermined values to detect the presence of an analyte in the material sample 18.

Figure 2:
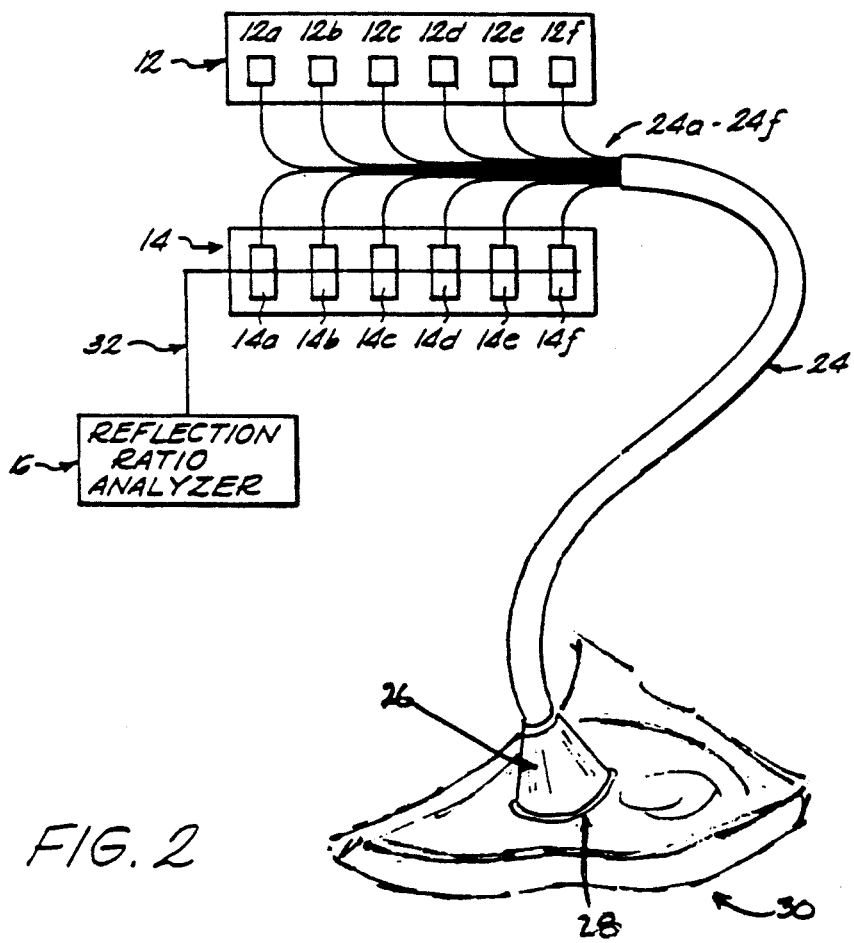
FIG. 2 is a schematic diagram of the apparatus according to the invention particularly adapted for non-destructive detection of analytes in a food sample.

An analytic apparatus 10 according to the invention particularly adapted to provide a system for detecting analytes in a food material is shown in FIG. 2. As can be seen from FIG. 2, laser diode elements 12a-12f comprise a multiple wavelength illumination source 12 whereby they provide light at a series of material analysis wavelengths (e.g. from about 500 nm to about 2000 nm). Diode elements 12a-12f each transmit a predetermined wavelength of light via corresponding optical fiber elements 24a-24f and sampling head 26, to a material sample 28. The discrete wavelengths of laser light preferably passes through the surface of the material 30 to illuminate a region 28 of material.

A fraction of the transmitted light is reflected back from illuminated region of the material 28 along optical fiber elements 24a-24f. (Each optical fiber element 24a-24f carries a reflected light signal having the same wavelength as the light originally transmitted along it.) Diode detectors 14a-14f receive the reflected light from the optical fiber elements 24a-24f and convert these light waves into a series of electrical signals indicative of the intensity of each of the reflected wavelengths of light received from illuminated region 28. For example, if laser diode element 12a originally transmitted light of wavelength 500 nm along optical fiber element 14a, then optical fiber element 14a will carry reflected light of wavelength 500 nm back to diode detector element 22a.

As shown in FIG. 2, diode detector elements 14a-14f transmit the electrical signals indicative of the intensity of the reflected light to reflection ratio analyzer 16 along electrical connection 32. Analyzer 16 compares the electrical signals received from diode detector elements 14a-14f to derive a reflectance ratio for at least two of the transmitted wavelengths of light, such that the ratio can be compared to predetermined values to detect the presence of an analyte in the illuminated region 28 of material 30. Analyzer 16 can also comprise means for quantifying the concentration of the detected analyte.

Figure 3:
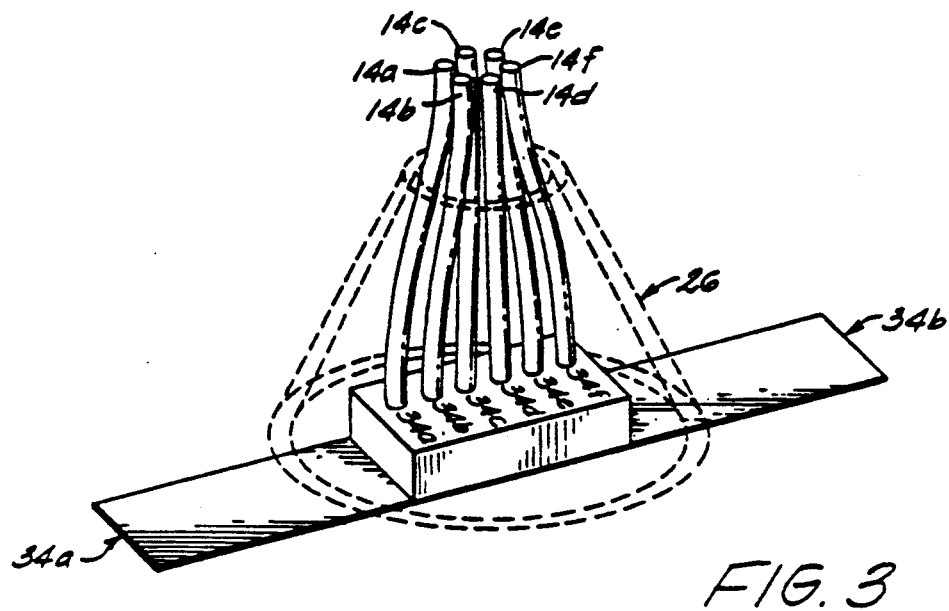
FIG. 3 is a detailed view of the sampling head assembly of the apparatus of FIG. 3.

FIG. 3 shows a more detailed view of the sampling head 26 of FIG. 2. As can be seen from FIG. 3, optical fiber elements 24a-24f of optical fiber bundle 24 are adapted to extend through a corresponding set of holes 32a-32f in the sampling head 26 thus facilitating alignment of optical fiber elements 24a-24f with the material 30. Sampling head 26 can also comprise taping flanges 34a and 34b located at opposed ends of sampling head 26, providing a means for affixing sampling head 26 with a surface of material 30.

Figure 4:
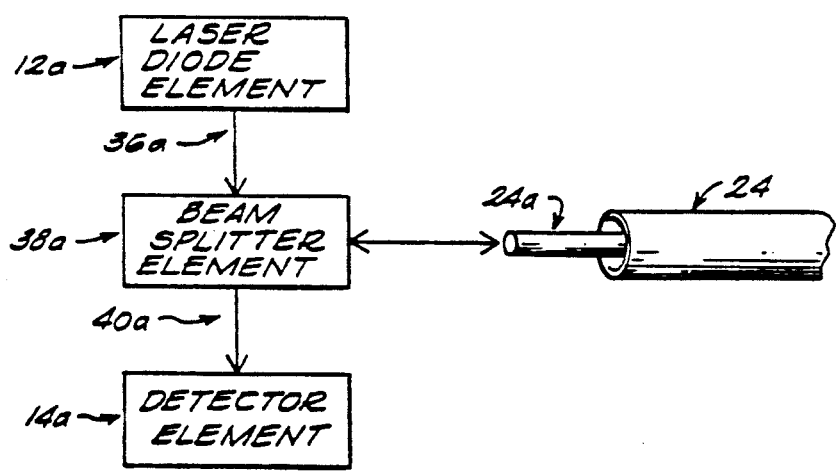
FIG. 4 is a more detailed illustration of an individual optical fiber and its connection to an illumination source and a detector element according to the invention.

FIG. 4 is a more detailed illustration of an individual optical fiber 24a and its connection to an illumination source 12a and a detector element 14a according to the invention. Since each of optical fiber elements 24a-24f is identically adapted, only optical fiber element 24a is shown. Laser diode element 12a is connected to optical fiber element 24a via optical fiber element 36a through optical splitter 38a. Diode detector element 14a is connected to optical fiber element 24a via optical fiber element 40a, also through optical splitter 38a. Optical splitter element 38a (and corresponding elements 38b-38f, not shown) enable dual usage of optical fiber elements 24a-24f so that the light transmitted from laser diode elements 12a-12f and the light reflected back from the illuminated region 28 travels along the same optical fiber elements 24a-24f.

Figure 5:
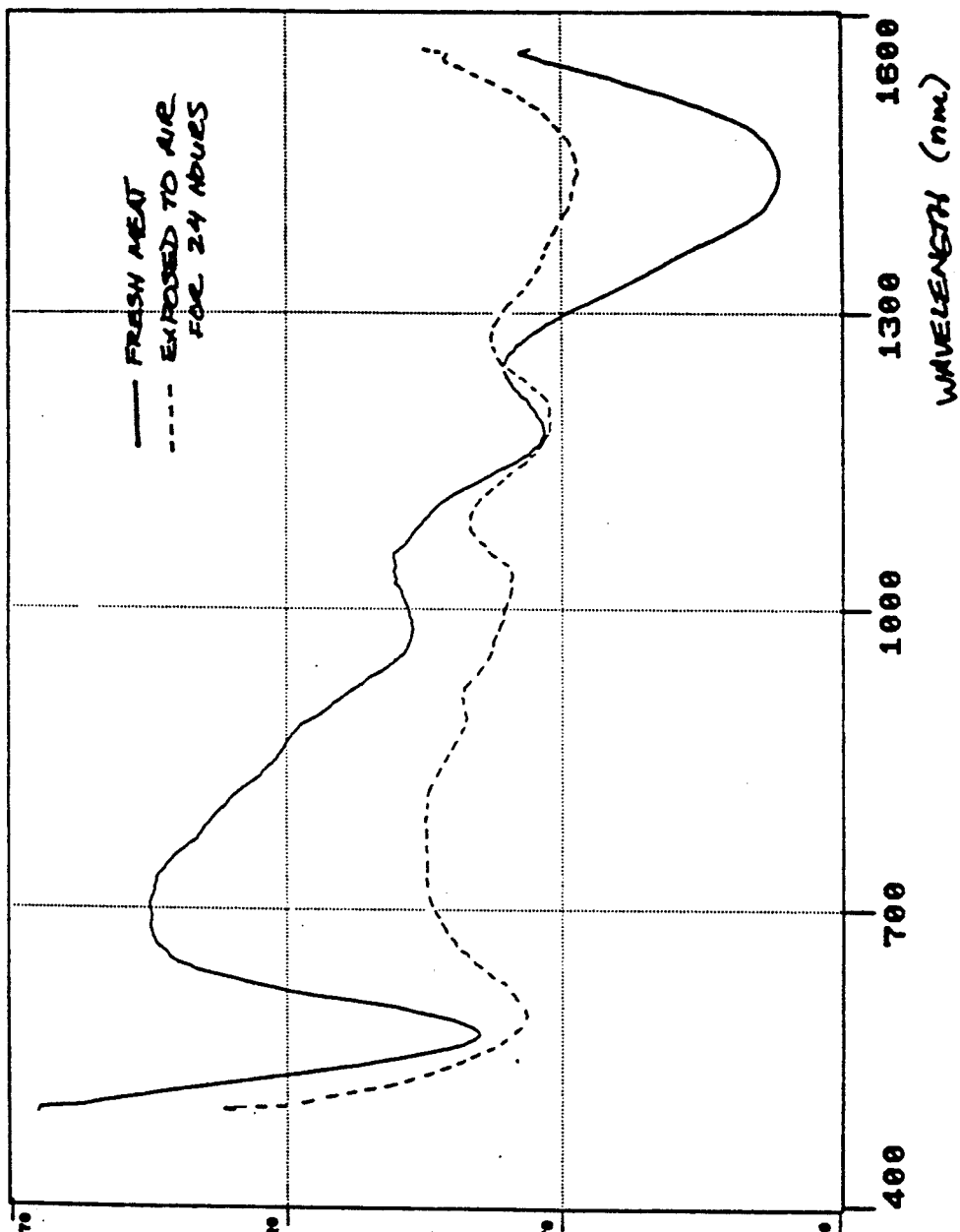
FIG. 5 is a graph of reflectivity versus wavelength for a meat sample exposed to air at room temperature overnight, demonstrating the analytical techniques of the present invention.

FIG. 5 is a graph of the reflectance spectrum of fresh meat (shown by the solid curve) and the same meat sample after exposure to air at room temperature for 24 hours (shown by the dashed curve). The wavelength of source light is shown along the x-axis and the intensity of the light reflected back from the hemoglobin is shown along the y-axis. Considering the measured ratio of the reflected light for the fresh and spoiled meat samples at wavelengths of about 700 nm and about 1200 nm, and referring to FIG. 5, the intensity of the reflected light measured at 700 nm divided by the intensity of the reflected light measured at 1200 nm in the case of the fresh meat sample is substantially greater than one. However, in the case of one day old sample, the same ratio is only slightly greater than one. Such a clearly differentiable ratio is readily detectable, and the exact ratio can be correlated with the actual freshness of the material under analysis. Similar, or in some cases even greater differences are observed in the cooking of meats, particularly red meats.

Figure 6:
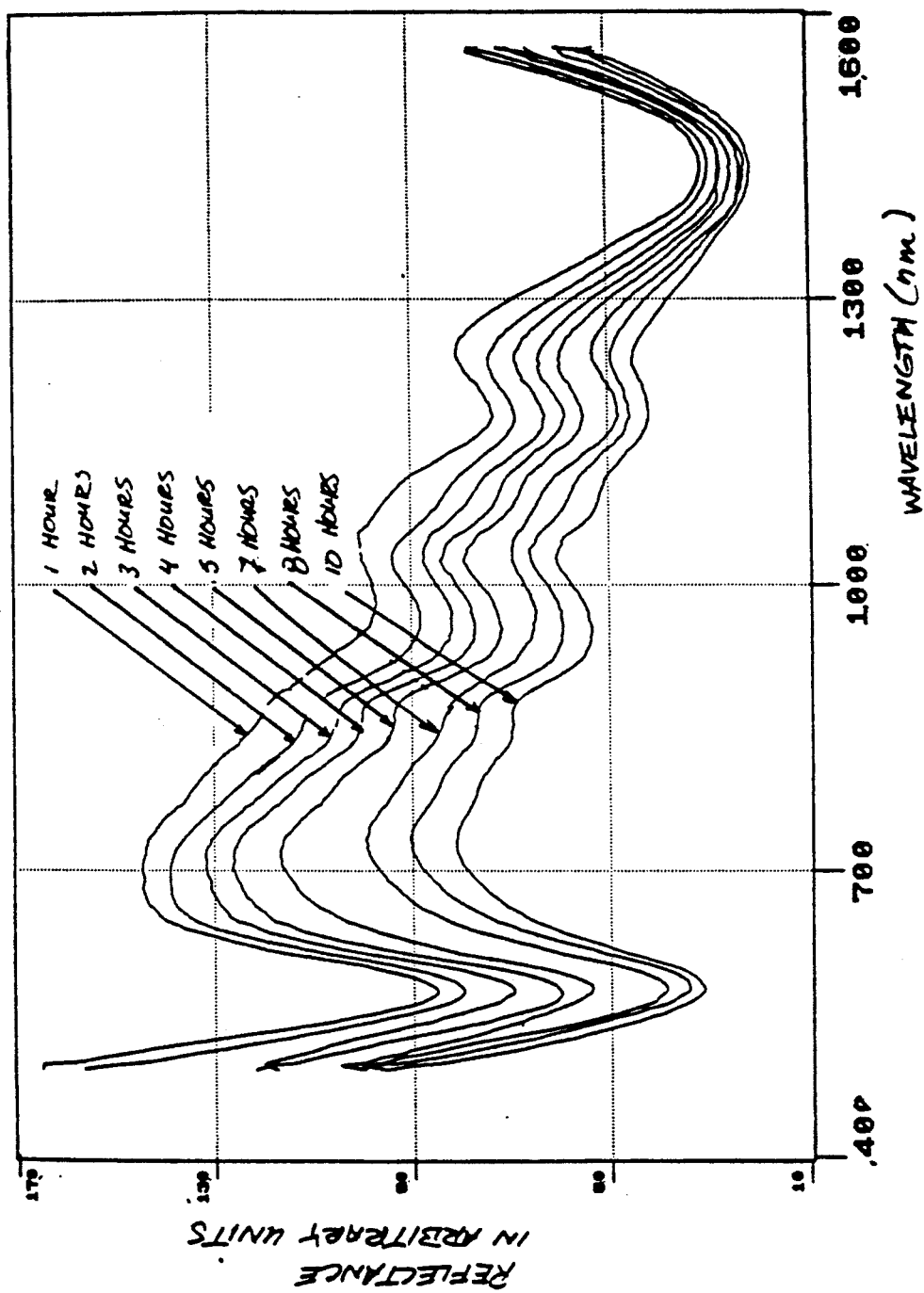
FIG. 6 is a similar graph of reflectivity versus wavelength taken at hourly intervals on a meat sample exposed to air at room temperature, further demonstrating the analytical techniques of the present invention.

This same phenomenon of changing reflectance ratios is further illustrated in FIG. 6 where reflectance spectra for a meat sample exposed to air at room temperature is shown at hourly intervals. Again, it can be seen that the peak at about 700 nm drops off rapidly as the sample begins to spoil and a comparison of reflectance ratios at about 700 and 1200 nm yields a reliable and quantitative measure of the freshness of the meat sample.

While FIGS. 5-6 illustrate the invention as applied to measurement of food freshness or preparatory state, in alternative embodiments the invention is suitable for detecting components of other materials such as contaminants in cooking oils, moisture in fuels, alcohol content in beverages, and blood analysis.

As indicated above, the invention may be embodied in other specific forms without departing from the spirit or the essential characteristics thereof. The present embodiment is to be considered as illustrative and not restrictive. The scope of the invention is indicated by the appended claims, rather than by the foregoing description, and all changes which come within the meaning and range of equivalent of the claims are therefore intended to be embraced therein.

What is claimed is:

1. An apparatus for detecting an analyte in a red meat sample, said analyte indicative of the freshness grade of said red meat sample, comprising:

illuminating means for illuminating said red meat sample, said illumination means having at least a first and second monochromatic laser diode, each said laser diode emitting radiation at a respective assigned wavelength, said first diode emitting radiation at about 700 nm and said second diode emitting radiation at about 1200 nm;

detector means for detecting light reflected from said red meat sample at said first and second wavelengths of about 700 nm and about 1200 nm, and for converting said detected light into electrical signals, said signals being indicative of the intensity of said reflected light at each detected wavelength; and an analyzing means for receiving and comparing said electrical signals to derive a reflectance ratio for said first and second wavelengths of about 700 nm and about 1200 nm, such that said ratio can be compared with predetermined values to detect the presence of said analyte in said sample.

2. The apparatus of claim 1 wherein said analyzing means further comprises means for quantifying the concentration of said analyte in said red meat sample.

3. A method for monitoring the composition of a red meat sample comprising:

illuminating said red meat sample at a plurality of wavelengths, including at least a first of said wavelengths being about 700 nanometers and at least a second of said wavelengths being about 1200 nanometers;

detecting light reflected from said red meat sample and converting said detected light into electrical signals indicative of the intensity of said reflected light at a plurality of wavelengths, including said first and second wavelengths about 700 nanometers and about 1200 nanometers;

analyzing said electrical signals to derive a reflectance ratio for said first and second wavelengths; and comparing said ratio to a predetermined value to detect the presence of an analyte in said red meat sample.

4. The method of claim 3 wherein the step of analyzing said signals further comprises quantifying the concentration of an analyte in said red meat sample.

* * * * *